US006234987B1

(12) United States Patent
Chen

(10) Patent No.: US 6,234,987 B1
(45) Date of Patent: May 22, 2001

(54) FOOT HEEL MASSAGING DEVICE

(76) Inventor: Hsing-Yu Chen, No. 466, Pu Zi Street, Feng Yuan City, Taichung Hsien (TW)

( * ) Notice: Subject to any disclaimer, the term of this patent is extended or adjusted under 35 U.S.C. 154(b) by 0 days.

(21) Appl. No.: 09/258,903

(22) Filed: Mar. 1, 1999

(51) Int. Cl.[7] .............................. A61H 7/00; A43B 21/24; A61F 5/14

(52) U.S. Cl. .............................. 601/85; 601/86; 601/112; 601/136; 36/92; 36/39; 36/69; 36/141

(58) Field of Search .............................. 601/15, 18, 22, 601/27, 28, 50, 86, 85, 112, 114, 134–8; 36/92, 117.3–117.5, 28, 37, 39, 69, 141

(56) References Cited

U.S. PATENT DOCUMENTS 2,067,979 * 1/1937 Newton .
3,220,405 * 11/1965 Bross .
4,694,831 * 9/1987 Seltzer .
5,502,901 * 4/1996 Brown .
5,689,902 * 11/1997 Juang .

FOREIGN PATENT DOCUMENTS

1331507 * 8/1987 (SU) .
1540825 * 2/1990 (SU) .
1666125 * 7/1991 (SU) .

* cited by examiner

*Primary Examiner*—Danton D. DeMille
(74) *Attorney, Agent, or Firm*—Browdy & Neimark

(57) ABSTRACT

A foot heel massaging device is located in the heel of a shoe to massage the foot heel of a person wearing the shoe. The device consists essentially of a fixed member located fixedly in the shoe heel, a movable member located movably on the fixed member and provided with a plurality of massaging knobs, a confining member for confining the fixed member and the movable member, and two magnets located respectively in the fixed member and the movable member such that the like magnetic poles of the two magnets are opposite to each other to bring about a repulsion force to cause the movable member to move away from the fixed member at the time when the movable member is relieved of an external force exerting thereon.

13 Claims, 3 Drawing Sheets

FOOT HEEL MASSAGING DEVICE

FIELD OF THE INVENTION

The present invention relates generally to a sole massager, and more particularly to a massager that is disposed in the shoe for massaging the foot heel.

BACKGROUND OF THE INVENTION

It is believed that the blood circulation of the human body can be promoted by stimulating the soles in such a manner that a person walks on a path which is paved with pebbles, or on a knobbed pad. However, such a practice as described above must be done persistently to realize the massaging effect on the blood circulation. Most people do not have time to do the practice regularly and persistently.

SUMMARY OF THE INVENTION

It is therefore the primary objective of the present invention to provide a sole massaging device which is disposed in the shoes for stimulating the circulatory system of a person wearing the shoes.

It is another objective of the present invention to provide a sole massaging device which is disposed in the shoes for dual purposes of serving as a sole massager and a shock absorber.

The objectives, features and functions of the present invention will be readily understood upon a thoughtful deliberation of the following detailed description of a preferred embodiment of the present invention with reference to the accompanying drawings.

DETAILED DESCRIPTION OF THE INVENTION

Figure 1:
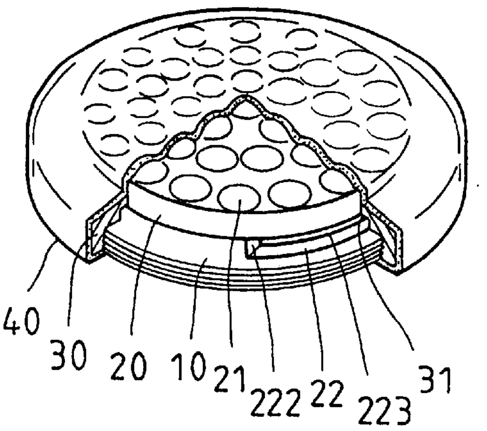
FIG. 1 shows a partial sectional view of the preferred embodiment of the present invention in combination.
Figure 2:
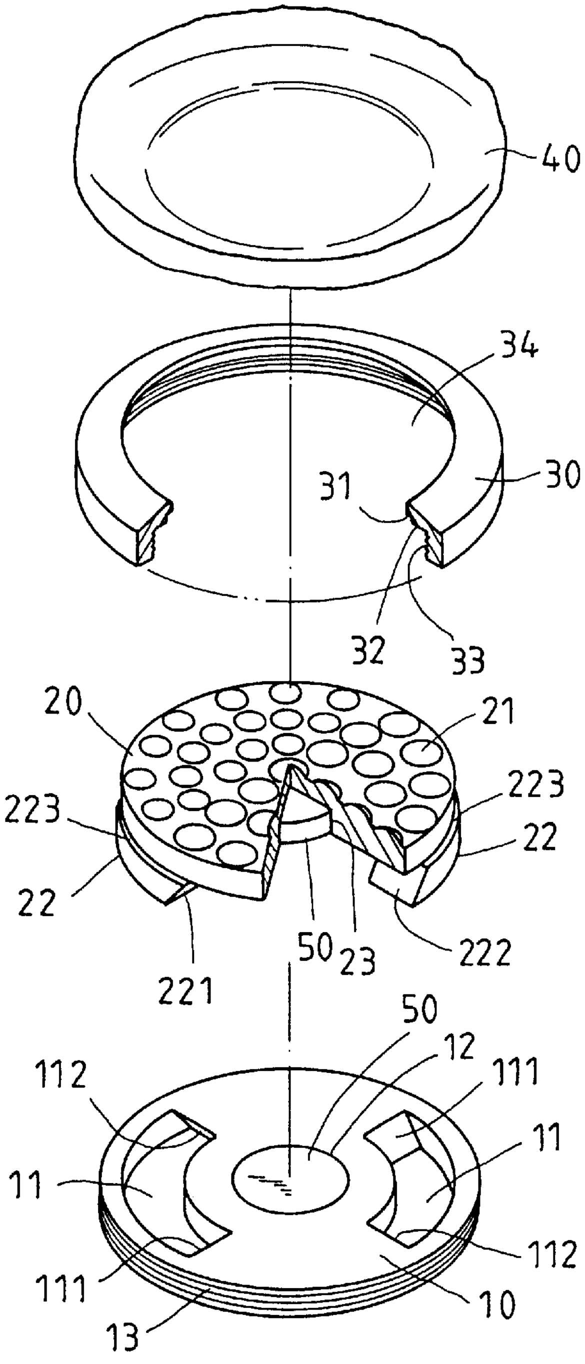
FIG. 2 shows a partial exploded view of the preferred embodiment of the present invention.

As shown in FIGS. 1 and 2, a sole massaging device of the present invention comprises the component parts which are described hereinafter.

A fixed member 10 is made of a metal or plastic material. The fixed member 10 embodied in the present invention is made of an aluminium alloy by casting and is provided with two guide portions 11 opposite in location to each other or forming together an angle of 120 or 90 degrees. The guide portions 11 are provided at one end thereof with a guide surface 111 having an inclination, such as 45 degrees and others. The fixed member 10 is provided at its center with a round slot 12, and at its peripheral wall with threads 13. The fixed member 10 is located fixedly in the heel of a shoe.

Figure 4:
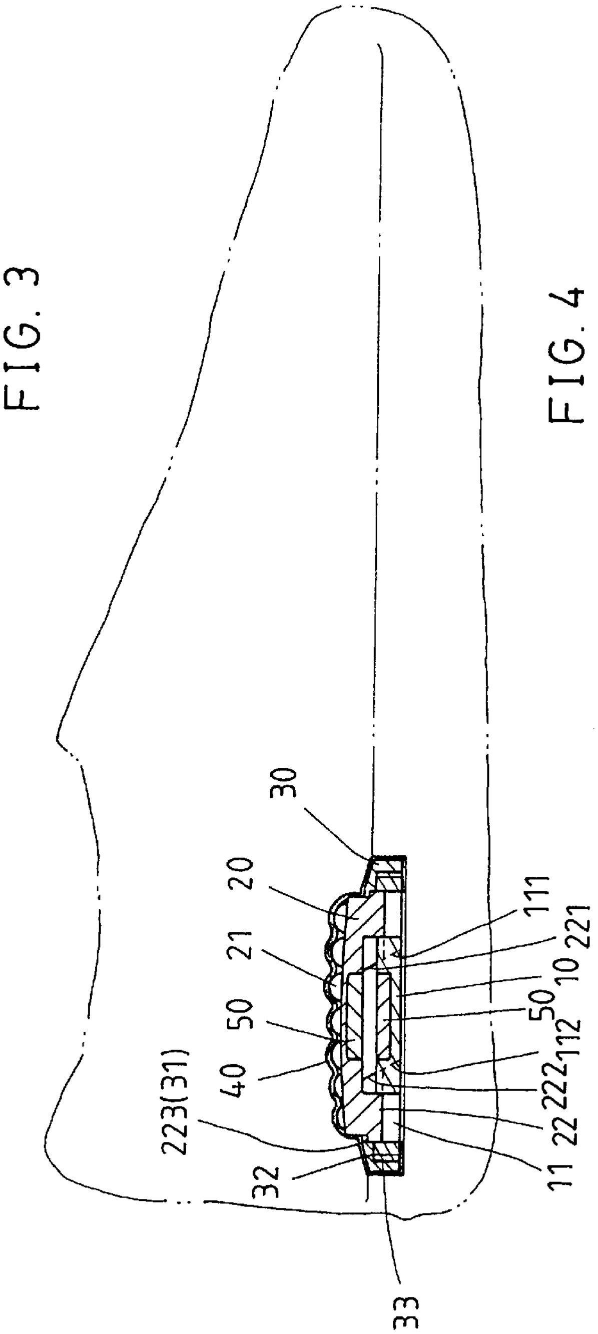
FIG. 4 shows a sectional view taken along the direction indicated by a line 4—4 as shown in FIG. 3.
Figure 6:
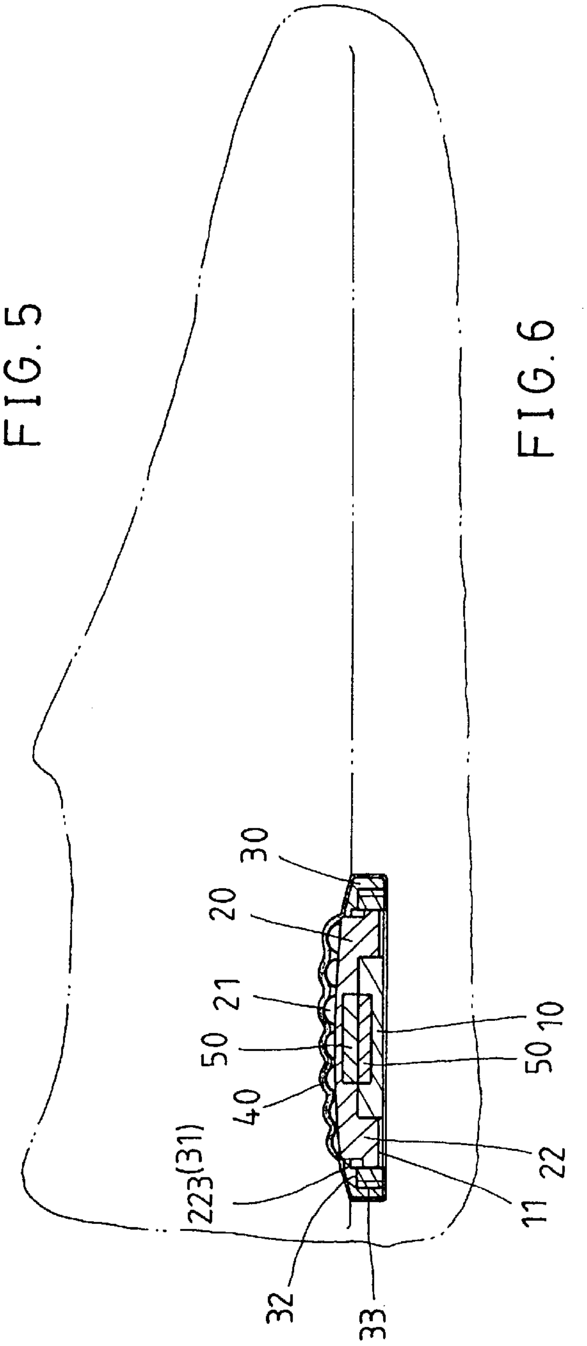
FIG. 6 shows a sectional view taken along the direction indicated by a line 6—6 as shown in FIG. 5.

A movable member 20 is corresponding in shape to the fixed member 10 and is made of a metal or plastic material. The movable member 20 is provided in the upper surface thereof with a plurality of knobs 21, and in the underside thereof with a plurality of guide portions 22 corresponding in number and shape to the guide portions 11 of the fixed member 10. Each guide portion 22 is provided at both ends thereof with two guide surfaces 221 and 222 each having an inclination of 45 degrees. One of the two guide surfaces 221 and 222 faces upward, whereas other of the two guide surfaces faces downward. The movable member 20 is joined with the fixed member 10 such that the two guide portions 22 are inserted into the two guide portions 11 of the fastening member 10, and that the movable member 20 is capable of turning in relation to the fixed member 10, thanks to the cooperation between the guide surfaces 111 and 221, and the cooperation between the guide surfaces 112 and 222, as shown in FIGS. 4 and 6. The two guide portions 22 have a shoulder surface 223 which is jutted out of the body of the movable member 20. The body of the movable member 20 is provided at the center of the underside thereof with a round slot 23.

A confining member 30 is made of a metal or plastic material. The confining member 30 has a cross section of an inverted stepped construction, with the inner top of the innermost side being provided with a confining surface 31, with the middle being provided with a shoulder surface 32, and with the inner peripheral wall being provided with a thread 33. The confining member 30 is joined with the fixed member 10 such that the thread 33 is engaged with the thread 13 of the fixed member 10, and that the shoulder surface 32 is rested on the body of the fixed member 10, and further that the confining surface 31 retains the shoulder surface 223 of the movable member 20 so as to enable the knobs 21 of the movable member 20 to jut out of the center hole 34 of the confining member 30.

A protective jacket 40 is made of a rubber or emulsion material and is fitted over the confining member 30 to protect the massaging device. The protective jacket 40 is an optional element.

Two magnetic members 50 are located respectively in the round slot 12 of the fixed member 10 and the round slot 23 of the movable member 20 such that the like magnetic poles of the two magnetic members 50 (magnets) are adjacent in location to each other, thereby enabling the movable member 20 to remain apart from the fixed member 10 by virtue of the repulsion force brought about by the like magnetic poles of the two magnets 50. The movable member 20 can be forced back down to join with the fixed member 10 by an external force exerting on the movable member 20, as shown in FIG. 6.

Figure 3:
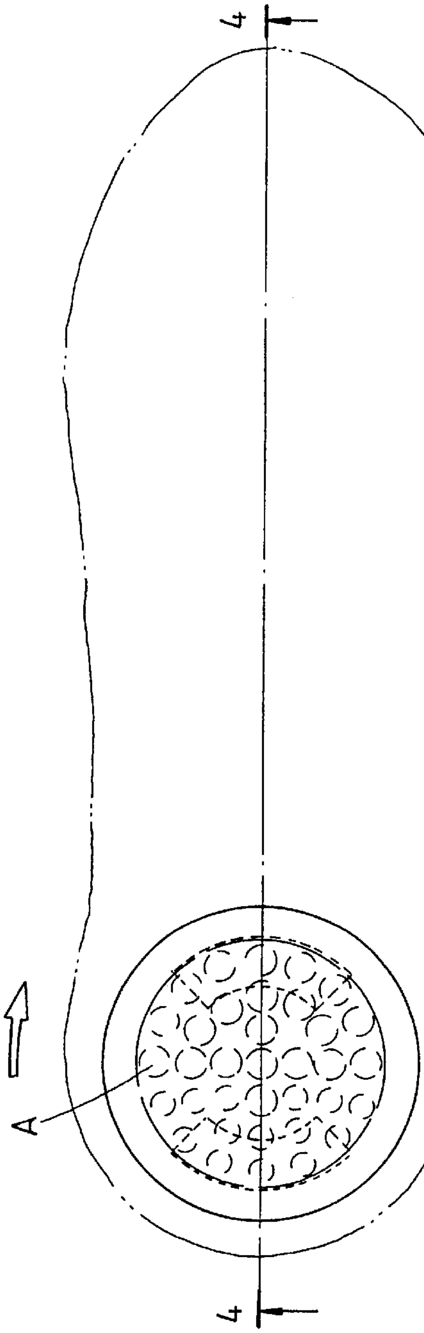
FIG. 3 shows a top view of the preferred embodiment of the present invention in conjunction with a shoe.
Figure 5:
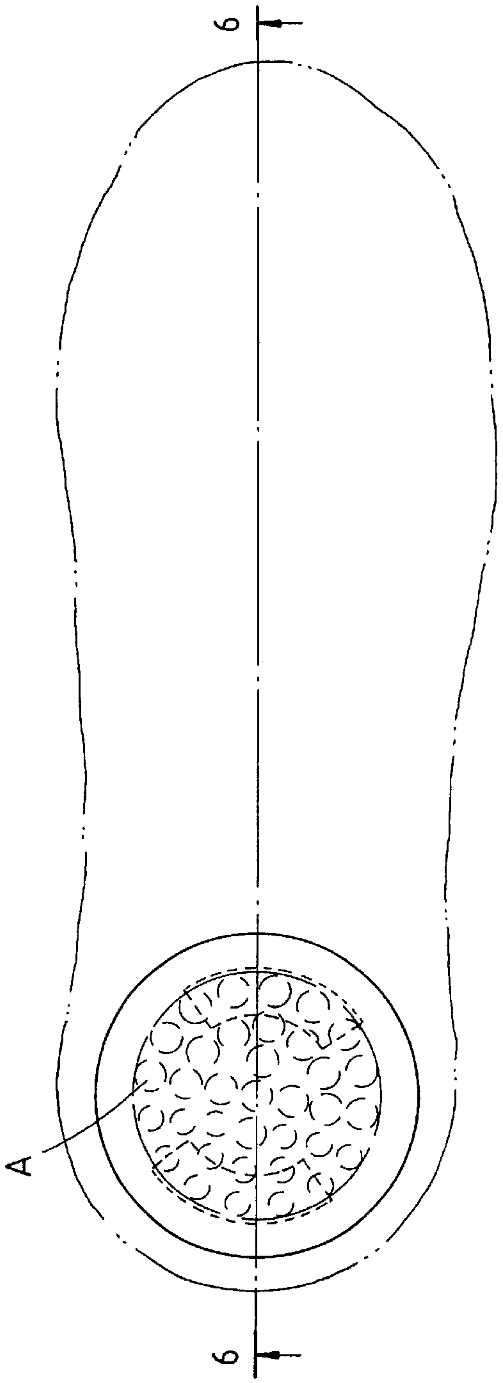
FIG. 5 is a top view showing that the device of the present invention is compressed and rotated angularly.

The device of the present invention is disposed in the heel of a shoe for massaging the foot heel. As illustrated in FIGS. 5 and 6, as the movable member 20 is exerted on by the force of a foot heel, the movable member 20 is forced to move down to join with the fixed member 10 such that the movable member 20 is turned an angle because of the cooperative action of the inclined guide surfaces 111 and 221. As a result, the knobs 21 of the movable member 20 are moved from the "A" position in FIG. 3 to the "A" position in FIG. 5, thereby enabling the knobs 21 to make contact with the foot heel. As the knobs 21 are pressed by the foot heel, the knobs 21 are twisted so as to bring about the effect of massaging the foot heel, as well as the effect of absorbing the shock. As soon as the movable member 20 is relieved of the force exerting thereon, the movable member 20 is caused to move away from the fixed member 10 by virtue of the repulsion force of the two magnets 50. In the meantime, the movable member 20 turns back to its original position, thanks to the cooperative action of the guide surfaces 112 and 222.

What is claimed is:

1. A foot heel massaging device consisting essentially of:

a fixed member located fixedly in the heel of a shoe;

a movable member located movably on said fixed member such that said movable member can be caused by an external force to join fully with said fixed member;

a confining member fitted over said fixed member for confining movement of said movable member; and two magnetic members located respectively in said fixed member and said movable member such that the like magnetic poles of said two magnetic members are adjacent in location to each other;

wherein said fixed member has at least one first guide portion and said movable member has at least one second guide portion corresponding in location and shape to said first guide portion, and wherein said first guide portion of said second guide portion cooperate to cause a first plane of said movable member to turn at an angle relative to a parallel second plane of said fixed member when said movable member is exerted on by an external force applied perpendicular to said first plane to join fully with said fixed member.

2. The massaging device as defined in claim 1, wherein said guide portion of said fixed member has two inclined guide surfaces located at both ends thereof such that said two inclined surfaces face in opposite directions; and wherein said guide portion of said movable member is retainable in said guide portion of said fixed member and is provided with two inclined guide surfaces located at both ends thereof such that said two inclined guide surfaces of said movable member cooperate with said two inclined guide surfaces of said fixed member to cause said movable member to turn said angle.

3. The massaging device as defined in claim 1, wherein said movable member is provided in an upper side thereof with a plurality of massaging knobs.

4. The massaging device as defined in claim 1, wherein said confining member is provided with a center hole; and wherein said fixed member and said movable member are confined by said confining member such that said movable member is partially jutted out of said center hole of said confining member.

5. The massaging device as defined in claim 4, wherein said confining member has a cross section of an inverted stepped construction, a confining surface, a thread, and a shoulder surface located between said confining surface and said thread; wherein said fixed member is provided in an outer peripheral wall thereof with a thread which is engaged with said thread of said confining member at the time when said fixed member is confined by said confining member; and wherein said guide portion of said movable member is provided with a shoulder surface which is retained by said confining surface of said confining member at the time when said movable member is confined by said confining member.

6. The massaging device as defined in claim 1, wherein said fixed member comprises two of said first guide portion opposite in location to each other.

7. The massaging device as defined in claim 1, wherein said fixed member comprises two of said first guide portions which are arranged to form together an angle of 120 degrees.

8. A foot heel massaging device consisting essentially of:

a fixed member located fixedly in the heel of a shoe;

a movable member located movably on said fixed member such that said movable member can be caused by an external force to join fully with said fixed member;

a confining member fitted over said fixed member for confining movement of said movable member; and two magnetic members located respectively in said fixed member and said movable member such that the like magnetic poles of said two magnetic members are adjacent in location to each other;

wherein said fixed member has at least one first guide portion; wherein said movable member comprises at least one second guide portion corresponding in location and shape to said first guide portion, and wherein said first guide portion of said second guide portion cooperate to cause said movable member to turn at an angle when said movable member is exerted on by an external force to join said movable member fully with said fixed member;

wherein said guide portion of said fixed member has two inclined guide surfaces located at both ends thereof such that said two inclined guide surfaces located at both ends thereof such that said two inclined surfaces face in opposite directions; and wherein said guide portion of said movable member is retainable in said guide portion of said fixed member and is provided with two inclined guide surfaces located at both ends thereof such that said two inclined guide surfaces of said movable member cooperate with said two inclined guide surfaces of said fixed member to cause said movable member to turn said angle.

9. The massaging device as defined in claim 8, wherein said movable member is provided in an upper side thereof with a plurality of massaging knobs.

10. The massaging device as defined in claim 8, wherein said confining member is provided with a center hole; and wherein said fixed member and said movable member are confined by said confining member such that said movable member is partially jutted out of said center hole of said confining member.

11. The massaging device as defined in claim 10, wherein said confining member is provided with a center hole; and wherein said fixed member and said movable member are confined by said confining member such that said movable member is partially jutted out of said center hole of said confining member.

12. The massaging device as defined in claim 8, wherein said fixed member comprises two of said first portion adjacent in location to each other.

13. The massaging device as defined in claim 8, wherein said fixed member comprises two of said first guide portion which are arranged to form together an angle of 120 degrees.

* * * * *